US009586056B2

(12) United States Patent
Zucker (10) Patent No.: US 9,586,056 B2
(45) Date of Patent: Mar. 7, 2017

(54) COMBINATION THERAPY FOR TREATING CANCER AND METHOD FOR TREATING CANCER USING A COMBINATION THERAPY

(71) Applicant: Shoshanna Zucker, Williamsville, NY (US)

(72) Inventor: Shoshanna Zucker, Williamsville, NY (US)

(73) Assignee: Haniva LLC, Williamsville, NY (US)

( * ) Notice: Subject to any disclaimer, the term of this patent is extended or adjusted under 35 U.S.C. 154(b) by 0 days.

(21) Appl. No.: 14/665,940

(22) Filed: Mar. 23, 2015

(65) Prior Publication Data

US 2016/0001052 A1    Jan. 7, 2016

Related U.S. Application Data

(60) Provisional application No. 62/020,800, filed on Jul. 3, 2014.

(51) Int. Cl.
| | |
|---|---|
| *A61M 37/00* | (2006.01) |
| *A61K 38/00* | (2006.01) |
| *A61K 31/35* | (2006.01) |
| *A61N 1/00* | (2006.01) |
| *A61B 18/04* | (2006.01) |
| *A61N 1/44* | (2006.01) |
| *A61K 31/53* | (2006.01) |
| *A61K 33/00* | (2006.01) |

(52) U.S. Cl.
CPC ................ *A61N 1/44* (2013.01); *A61K 31/53* (2013.01); *A61K 33/00* (2013.01); *A61M 2037/0007* (2013.01)

(58) Field of Classification Search
None
See application file for complete search history.

(56) References Cited

U.S. PATENT DOCUMENTS

| 7,306,801 | B2 | 12/2007 | Caligiuri et al. | |
|---|---|---|---|---|
| 2012/0045501 | A1 | 2/2012 | Huang et al. | |
| 2012/0087913 | A1* | 4/2012 | Lee ...................... | A61K 31/167 424/133.1 |
| 2012/0135390 | A1 | 5/2012 | Clyne et al. | |
| 2012/0296265 | A1 | 11/2012 | Dobrynin et al. | |

OTHER PUBLICATIONS

Hong et al.; Invest. New Drugs (2011) 29:401-410.*
Zucker et al.; Cancer Biology & Therapy; 13:13, 1299-1306; Nov. 2012.*
Lucas, R. et al., "Global Burden of Disease of Solar Ultraviolet Radiation", Environmental Burden of Disease Series, No. 13, News Release, World Health Organization, 2006.
Fridman, et al., "Floating Electrode Dielectric Barrier Discharge Plasma in Air Promoting Apoptotic Behavior in Melanoma Skin Cancer Cell Lines", Plasma Chemistry & Plasma Processing, vol. 27, Issue 2, pp. 163-176, Mar. 2, 2007.
Sensenig, et al., "Non-thermal Plasma Induces Apoptosis in Melanoma Cells via Production of Intracellular Reactive Oxygen Species", Annals of Biomedical Engineering, vol. 39, Issue 2, pp. 674-687, Oct. 29, 2010.
Nuccitelli, et al., "Nanosecond Pulsed Electric Fields Cause Melanomas to Self-destruct", Biochem Biophys Res Commun 343, pp. 351-360, May 5, 2006.
Qin, et al., "Molecular Dynamics Analysis of High Electric Pulse Effects on Bilayer Membranes Containing DPPC and DPPS", Plasma Science, IEEE Transactions, vol. 34, Issue 4, pp. 1405-1411, 2006.
Laroussi, "The Biomedical Applications of Plasma: A Brief History of the Development of a New Field of Research", Plasma Science, IEEE Transactions, vol. 36, pp. 1612-1614, 2008.
Fridman, et al., "Blood Coagulation and Living Tissue Sterilization by Floating-Electrode Dielectric Barrier Discharge in Air", Plasma Chemistry & Plasma Processing, vol. 26, Issue 4, pp. 425-442, Aug. 2006.
Vankov, et al., "Nanosecond Plasma-mediated Electrosurgery with Elongated Electrodes", Journal of Applied Physics, vol. 101, pp. 124701-124707, Jun. 19, 2007.
Stoffels, et al., "Cold Atmospheric Plasma: Charged Species and Their Interactions with Cells and Tissues", Plasma Science, IEEE Transactions, vol. 36, Issue 4, pp. 1441-1457, 2008.
Gaunt, et al., "Bactericidal Action of the Reactive Species Produced by Gas-Discharge Nonthermal Plasma at Atmospheric Pressure: A Review", IEEE Transactions on Plasma Science, vol. 34, No. 4, pp. 1257-1269, Aug. 2006.
Kim, et al., "Air Plasma Coupled with Antibody-conjugated Nanoparticles: A New Weapon Against Cancer", J. Phys. D: Appl. Phys., vol. 42, pp. 032005-032010, Dec. 31, 2008.
Esser, et al., "Towards Solid Tumor Treatment by Nanosecond Pulsed Electric Fields", Technol. Cancer Res. Treat., vol. 8, No. 4, pp. 289-306, Aug. 2009.
Klaunig, et al., "The Role of Oxidative Stress in Carcinogenesis", Annual Rev. Pharmacol. and Toxicol., vol. 44, pp. 239-267, Feb. 2004.
Zucker, et al., "Abstract B18: Non-thermal Plasma, Tirapazamine, and Gap Junctions: A Novel Approach to Melanoma Therapy Through ROS induction", Cancer Research, Jul. 15, 2015.
Stoffels, et al., "Plasma Needle for In Vivo Medical Treatment: Recent Developments and Perspectives", Plasma Sources Sci. and Technol., vol. 14, No. 4, pp. S169-S180, Oct. 6, 2006.
Zirnheld, et al., "NonThermal Plasma Needle: Development and Targeting of Melanoma Cells", IEEE Transactions on Plasma Science, vol. 38, No. 4, pp. 948-952, Apr. 2010.
Nagasawa, et al., "Design, Synthesis and Biological Activities of Antiangiogenic Hypoxic Cytotoxin, Triazine-N-oxide Derivatives", Comp. Biochem. Physiol. A. Mol. Integr. Physiol., May 2002.
Onyenucheya et al., "Characterization of a Non Thermal Plasma Torch", Pulsed Power, International Conference—PPC, pp. 1022-1024, 2009.

(Continued)

*Primary Examiner* — Jeffrey T Palenik
(74) *Attorney, Agent, or Firm* — Simpson & Simpson, PLLC (57) ABSTRACT

A combination therapy for treating cancer including a DNA damaging agent deliverable to cancer cells and operatively arranged to activate only under a low oxygen condition and a non-thermal plasma deliverable to cancer cells. The non-thermal plasma and the DNA damaging agent individually and in conjunction promote cell toxicity.

19 Claims, 10 Drawing Sheets

(56) References Cited

OTHER PUBLICATIONS

Kang, et al., "Nonthermal Plasma Induces Head and Neck Cancer Cell Death: The Potential Involvement of Mitogen-activated Protein Kinase-dependent Mitochondrial Reactive Oxygen Species", Cell Death and Dis., Feb. 13, 2014.

Zhou, et al., "Gap Junction and Hemichannel-independent Actions of Connexins on Cell and Tissue Functions—An Update", FEBS Letters, vol. 588(8), pp. 1186-1192, Jan. 14, 2014.

Chandel, et al., "Mitochondrial Reactive Oxygen Species Trigger Hypoxia-induced Transcription", Proc. Natl. Acad. Sci. U S A., vol. 95(20), pp. 11715-11720, Sep. 1998.

Dorie, et al., "DNA Damage Measured by the Comet Assay in Head and Neck Cancer Patients Treated with Tirapazamine", Neoplasia, vol. 1(5), pp. 461-467, Nov. 5, 1999.

Zucker, S.N., et al., "Preferential Induction of Apoptotic Cell Death in Melanoma Cells as Compared with Normal Keratinocytes Using a Non-thermal Plasma Torch", Cancer Biology & Therapy 13:13, pp. 1299-1306, Nov. 2012.

\* cited by examiner

COMBINATION THERAPY FOR TREATING CANCER AND METHOD FOR TREATING CANCER USING A COMBINATION THERAPY

CROSS-REFERENCE TO RELATED APPLICATIONS

This application claims the benefit under §119(e) of U.S. Provisional Application No. 62/020,800, filed Jul. 3, 2014, which application is hereby incorporated by reference in its entirety.

FIELD OF THE INVENTION

The present invention relates generally to a combination therapy for cancer, and, more particularly, to a therapy including a non-thermal plasma and a DNA damaging agent that selectively promotes cancer cell death as compared with healthy cells.

BACKGROUND OF THE INVENTION

Melanoma is the most rapidly progressing malignancy in the United States, accounting for 75% of all skin cancer-associated deaths. Lucas, R. et al., "Global Burden of Disease of Solar Ultraviolet Radiation", Environmental Burden of Disease Series, No. 13, News Release, World Health Organization, 2006. Currently, a dielectric barrier discharge (DBD) device is being tested for the treatment of melanoma. DBD requires that the target tissue be placed between two metal plates that are used as typical type electrodes. Gregory, F. et al., "Floating Electrode Dielectric Barrier Discharge Plasma in Air Promoting Apoptotic Behavior in Melanoma Skin Cancer Cell Lines", Plasma Chemistry & Plasma Processing, Volume 27, Issue 2, pp 163-76, April 2007; Sensenig, R., et al., "Non-thermal Plasma Induces Apoptosis in Melanoma Cells via Production of Intracellular Reactive Oxygen Species", Annals of Biomedical Engineering, Volume 39, Issue 2, pp 674-87, February 2011. Multiple rapid pulses of DBD plasma therapy can cause electro-deformation of cells, which opens pores and disrupts cellular membranes. Nuccitelli, R., et al., "Nanosecond Pulsed Electric Fields Cause Melanomas to Self-destruct", Biochem. and Biophys. Res. Commun. 343, pp 351-360, 2006; Qin, H., et al., "Molecular Dynamics Analysis of High Electric Pulse Effects on Bilayer Membranes Containing DPPS and DPPS", Plasma Science, IEEE Transactions, Volume 34, Issue 4, pp 1405-11, 2006. Although surgical incision is still the best way to remove primary melanoma, there is still a need to target cells that escape surgical resection.

In recent years, atmospheric pressure non-thermal plasmas have been used in various medical applications. Laroussi, M., "The Biomedical Applications of Plasma: A Brief History of the Development of a New Field of Research", Plasma Science, IEEE Transactions, Volume 36, pp 1612-4, 2008. Since non-thermal plasmas do not give off heat they can be therapeutic. Non-thermal plasmas are non-toxic, and can promote sterilization.

Currently, non-thermal plasma is being investigated for its potential role in wound healing, tissue incision, protein destruction, cell and tissue modification, bacterial inactivation as well as cancer treatment. See, respectively, Fridman, G., et al., "Blood Coagulation and Living Tissue Sterilization by Floating-Electrode Dielectric Barrier Discharge in Air", Plasma Chemistry & Plasma Processing, Volume 26, Issue 4, pp 425-42, August 2006; Vankov, A. et al., "Nanosecond Plasma-mediated Electrosurgery with Elongated Electrodes", Journal of Applied Physics, Volume 101, pp 124701-7, 2007; Stoffels, E., et al., "Cold Atmospheric Plasma: Charged Species and Their Interactions with Cells and Tissues", Plasma Science, IEEE Transactions, Volume 36, Issue 4, pp 1441-57, 2008; Gaunt, L. F., et al., "Bactericidal Action of the Reactive Species Produced by Gas-Discharge Nonthermal Plasma at Atmospheric Pressure: A Review", Plasma Science, IEEE Transactions, Volume 34, Issue 4, pp 1257-69, 2006; Kim, G. C., et al., "Air Plasma Coupled with Antibody-conjugated Nanoparticles: A New Weapon Against Cancer", J. Phys. D: Appl. Phys., Volume 42, pp 032005-10, 2008; and Esser, A. T., et al., "Towards Solid Tumor Treatment by Nanosecond Pulsed Electric Fields", Technol. Cancer Res. Treat., Volume 8, Number 4, pp 289-306, August 2009.

Non-thermal plasma is an ionized gas with electron densities of $10^{11}$-$10^{14}$ [$1/cm^3$] and typical energies of 1-5 [eV]. Despite its high energy, non-thermal plasma exhibits near room temperature characteristics due to the low number density of electrons. Thus, non-thermal plasma is suitable for biological applications such as cell and tissue processing.

A plasma torch is a good source of reactive species, which have been shown to induce apoptosis due to the energetic electrons. Klaunig, J. E., et al., "The Role of Oxidative Stress in Carcinogenesis", Annual Rev. Pharmacol. and Toxicol., Volume 44, pp 239-67, February 2004. Recent studies have shown that non-thermal plasma can induce apoptosis to a limited extent. Gregory, F. et al., "Floating Electrode Dielectric Barrier Discharge Plasma in Air Promoting Apoptotic Behavior in Melanoma Skin Cancer Cell Lines", Plasma Chemistry & Plasma Processing, Volume 27, Issue 2, pp 163-76, April 2007.

Tirapazamine (referred to in the art as SR-4233 or TPZ) is an investigational drug for treating cancer. At sufficiently low levels of oxygen (referred to in the art as hypoxia), commonly found in solid tumors in humans, TPZ is activated to a toxic radical, causing cell death. It is characteristic of tumor cells to be resistant to treatments of radiotherapy and many anti-cancer drugs. TPZ is a powerful cytotoxic agent that encourages programmed cell death (referred to in the art as apoptosis) by inducing disruptions in single and double stranded DNA, as well as chromosomal breaks. Additionally, TPZ causes cells to become more sensitive to other ionizing radiation and other cytotoxic agents. As such, since TPZ is activated to its toxic form preferentially in the hypoxic areas of solid tumors, the benefits of the combination of TPZ with conventional anti-cancer treatments can be realized.

The chemical structure of TPZ is a benzotriazine di-N-oxide and its chemical name is 3-Aminobenzo[e][1,2,4]triazine 1,4-dioxide. It was originally formulated in 1972 for use as an herbicide, or weedkiller, and was not used clinically until over a decade later, in 1986. Clinically, TPZ has had only been minimally effective in trials; however, it has been used as a central compound in the development of several more recent compounds that have better cancer-treating properties.

As shown below, TPZ recycles between the inactive and active states:

TPZ     TPZ*

For example, P450 (cytochrome) oxidoreductase (otherwise known in the art as POR), 5-methyltetrahydrofolate-homocycstein methyltransferase reductase (otherwise known in the art as MTRR), and FAD-dependent oxidoreductase domain containing 2 (otherwise known in the art as FODRED2) can be suitable reductases; however, any suitable reductase known in the art is contemplated. For example, it is believed that tirapazamine produces hydroxyl and/or benzotriazinyl radicals as DNA damaging reactive species. The free radicals that are generated within the nucleus of the cell cause single- and double-stranded breaks in DNA, base damage, and cell death. Tirapazamine also inhibits topoisomerase II, an enzyme that is responsible for cutting both strands of a DNA helix simultaneously in order to manage super coils and avoid tangling of the chromosomes. The inhibition of this enzyme results in impaired ability of the cell to repair radiation-induced DNA breaks. Tirapazamine causes hypoxic cells to become more sensitive to the damaging effects of ionizing radiation. Moreover, tirapazamine can downregulate HIF-1α (or HIF1α) expression by decreasing HIF-1α protein synthesis. HIF-1α expression can indicate a cancer that is resistant to anticancer drugs, for example, topoisomerase I inhibitors. However, tirapazamine has not been used with non-thermal plasma clinically because of its toxicity.

Therefore, there is a long-felt need for a combination therapy for treating cancer. There is also a long-felt need for a combination therapy for treating cancer featuring a non-thermal plasma and a plasma torch. Additionally, there is a long-felt need for a therapy for primary and recurrent melanoma. Furthermore, there is a long-felt need for a combination therapy for treating cancer featuring a non-thermal plasma and a DNA damaging agent that promotes cell death where the DNA damaging agent is arranged to activate only under a low oxygen condition. There is also a long-felt need for a non-thermal plasma device which is versatile and effective at inducing apoptosis and/or necrosis and reactive oxygen species. Finally, there is a long-felt need for a combination therapy for treating cancer where the components of the therapy promote cell toxicity individually and in conjunction.

BRIEF SUMMARY OF THE INVENTION

According to aspects illustrated herein, there is provided a composition of matter thereinafter referred to as a combination therapy) for treating cancer including a DNA damaging agent deliverable to cancer cells and operatively arranged to activate only under a low oxygen condition and a non-thermal plasma deliverable to cancer cells. The non-thermal plasma and the DNA damaging agent individually and in conjunction promote cell toxicity.

According to aspects illustrated herein, there is provided a method of treating cancer in a patient using a combination therapy, comprising the following steps: delivering a DNA damaging agent to the treatment area, the DNA damaging agent operatively arranged to activate only under hypoxia and delivering a non-thermal plasma to the treatment area designated on the patient, the treatment area being infected with the cancer.

According to aspects illustrated herein, there is also provided a combination therapy for cancer including 1) non-thermal plasma and 2) a class of DNA damaging agents that are activated at hypoxic conditions including the drug, tirapazamine and any and all structural and/or functional derivatives. This invention includes but is not limited to application of molecular methodology and/or drugs that can modify the level of gap junctions. According to aspects illustrated herein, the atmospheric pressure non-thermal helium plasma torch based on the model by Stoffels, et al. is modified. Stoffels E., et al., "Plasma Needle for In Vivo Medical Treatment: Recent Developments and Perspectives", Plasma Sources Sci. and Technol., Volume 14, Number 4, pp S169-S80, 2006; Zirnheld, J. L., et al., "Non-Thermal Plasma Needle: Development and Targeting of Melanoma Cells", Plasma Science, IEEE Transactions, Volume 38, Issue 4, pp 948-52, 2010. In an example embodiment, the torch itself forms the first electrode and the second electrode is the target material (or whatever the plasma is interacting with: fluid, cells, etc.) or simply the atmosphere in the case of when the plasma jet is not interacting with a target. The primary advantage of using a plasma torch is the enhanced versatility for practical applications such as the potential to treat tumors virtually anywhere on the skin and possibly for the development of internal measuring devices.

The invention is a treatment for cancer using the induction of reactive oxygen species. Gap junctions can transfer signals promoting cell survival or cell death. Vinken Pharm Anal Acta 2011, 2:3, 2153-8. In an example embodiment, the combination therapy of the invention employs non-thermal plasma, tirapazamine, and gap junctions. Selective cell death of melanoma by apoptosis and/or necrosis can be achieved using a non-thermal plasma torch. This selective killing is likely induced by the greater susceptibility of melanoma cells to the multiple reactive oxygen species (ROS) produced by the NTP. Enhancing the selective killing of melanoma cells by NTP and increasing the affected surface area is desirable.

A primary object of the subject invention is to provide a combination therapy for treating cancer.

A further object of the subject invention is to provide a combination therapy for treating cancer featuring a non-thermal plasma and a plasma torch.

Yet another object of the subject invention is to provide a combination therapy for treating cancer featuring a non-thermal plasma and a DNA damaging agent that promotes cell death where the DNA damaging agent is arranged to activate only under a low oxygen condition.

Still another object of the subject invention is to provide a therapy for primary and recurrent melanoma.

A further object of the subject invention is to provide a combination therapy for treating cancer where the components of the therapy promote cell toxicity individually and in conjunction.

Yet another object of the subject invention is to provide a non-thermal plasma device, which is versatile and effective at inducing apoptosis and/or necrosis and reactive oxygen species.

These and other objects, features and advantages of the present invention will become readily apparent upon a reading and review of the following detailed description of the invention, in view of the appended drawings and claims.

BRIEF DESCRIPTION OF THE DRAWINGS

The nature and mode of operation of the present invention will now be more fully described in the following detailed description of the invention taken with the accompanying figures, in which.

DETAILED DESCRIPTION OF THE INVENTION

At the outset, it should be appreciated that like drawing numbers on different drawing views identify identical, or functionally similar, structural elements of the invention. It is to be understood that the invention as claimed is not limited to the disclosed aspects.

Furthermore, it is understood that this invention is not limited to the particular methodology, materials and modifications described and, as such, may, of course, vary. It is also understood that the terminology used herein is for the purpose of describing particular aspects only, and is not intended to limit the scope of the present invention as claimed. The combination therapy of the invention is described herein with respect to the extent of cell death between melanoma cells and normal skin cells or human epidermal keratinocytes (HEK) co-cultured experiments using soft agar. An example of the methodology employed in such experiments is detailed in Zucker, S. N., et al., "Preferential Induction of Apoptotic Cell Death in Melanoma Cells as Compared with Normal Keratinocytes Using a Non-thermal Plasma Torch", Cancer Biology & Therapy 13:13, pp 1299-1306, November 2012, which article is incorporated herein by reference in its entirety.

Unless defined otherwise, all technical and scientific terms used herein have the same meaning as commonly understood to one of ordinary skill in the art to which this invention pertains. It should be understood that any methods, devices or materials similar or equivalent to those described herein can be used in the practice or testing of the invention. Stably transfected melanoma cells can be used to show the functionality of the combination therapy of the invention; the transfected cells used herein express three different levels of gap junctions: endogenous low levels, increased levels, or an absence of gap junctions due to expression of a dominant negative mutant connexin protein. In all figures, the terms P, C, and T, respectively, refer to the level of gap junction expression of the cells in cells that are made to express plasmid alone (P), overexpression of connexin 43 to activate gap junctions (C), and overexpression of a dominant negative connexin 43 to block the function of gap junctions (T). The bars on the graphs represent the variability between the sample as calculated by the standard deviation.

Figure 1:
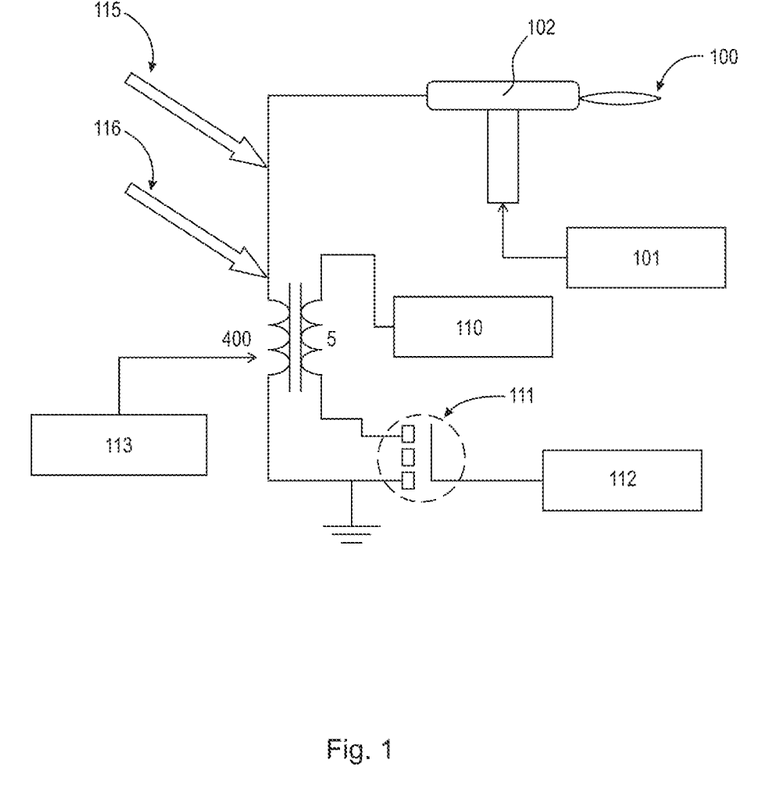
FIG. 1 is a schematic view of the plasma generating circuitry of the torch of the invention.

The combination therapy for treating cancer described herein includes a non-thermal plasma, which is deliverable to cancer cells. The circuitry of the generation of non-thermal plasma 100 is shown in FIG. 1. In an example embodiment, a beam of non-thermal plasma 100 is created by gas 101, preferably ionized helium gas, mixing with atmospheric gases being emitted from torch 102. In other words, in an example embodiment, non-thermal plasma 100 is generated by mixing helium gas 101 with atmospheric gases and ionizing the mixed gas by an electric field generated by torch 102 as further described herein. Any suitable alternative to helium gas can be used, for example, argon gas. Non-thermal plasma 100 induces reactive oxygen species (ROS), which contain non-radicals and radicals. It should be appreciated that melanoma cells have high intrinsic levels of superoxide anions that predispose the cells to apoptosis by non-thermal plasma. Thus, although plasma 100 is nontoxic to normal skin keratinocytes, plasma 100 is able to selectively target melanoma cells for apoptotic cell death.

Plasma generation device 102 depicted in FIG. 1 utilizes DC voltage from power supply 110. A suitable DC power supply is available from Transcat, Inc., 3 Vantage Point Drive, Rochester, N.Y., 14624, Model No.: Kenwood PD110-SAD. The DC voltage applied is switched through metal-oxide-semiconductor field-effect transistor (MOSFET) 111. A suitable MOSFET is available from RS Components Ltd., Birchington Road, Corby, Northants, NN17 9RS, UK, Manufacturers Part No. IRF540NPBF. MOSFET 111 is driven by function generator 112 operating at frequencies of 80-120 kHz, preferably. A suitable function generator is available from Tektronix, Inc., 14150 SW Karl Braun Drive, P.O. Box 500, Beaverton, Oreg., 97077, Model No.: TM503. This signal excites the primary windings of high frequency transformer 113 with a turns ratio of 5:400, preferably. A turns ratio of 4:400 may also be suitable. A suitable transformer made of high frequency powdered ferrite available from Ceramic Magnetics, Inc., 16 Law Drive, Fairfield, N.J., 07004, Model No.: CMD5005 can be used as the core for the transformer. It should be appreciated that any suitable ferrite or any magnetic ceramic usually using exotic magnetic materials to obtain extremely high permeability and excellent high frequency performance, for example, from 50 kHz to over 1 MHz, can be used. The secondary winding serves as the plasma-sustaining electrode which connects to plasma torch 102 via 50Ω (Ohms) BNC terminated coaxial cable 114 shown in FIG. 2.

Figure 2:
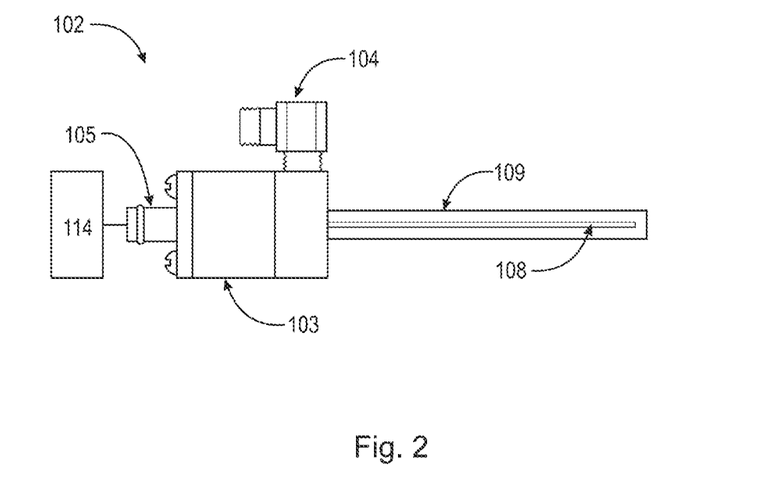
FIG. 2 is a schematic view of an example embodiment of the plasma torch device depicted in FIG. 1.

Voltage and current can be measured on the secondary winding with suitable voltage and current probes 115 and 116, respectively. For example, a suitable voltage probe, available from Tektronix, Inc., Model No.: P6015, and a suitable current probe, available from Tektronix, Inc., Model No.: P6022, can be used. The resulting waveforms can be digitized and analyzed using an oscilloscope available from Tektronix, Inc., Model No.: TDS 2014B. The frequency of the excitation signal is preferably approximately a 113 kHz square wave with a magnitude of preferably 12V. This forces the MOSFET into the saturation region allowing adequate current to excite the primary winding of the transformer. Voltage probe 115 records the potential of the secondary winding at approximately, preferably, 2.5 kV AC. Current probe 116 measures the current through the electrode with plasma formation at approximately, preferably, 1.5 mA; the power is calculated to be less than 1 W, approximately, preferably. It should be appreciated that plasma 100 can be generated using torch 102 at a frequency of 112-117 kHz with a flow rate of 3-4.7 L/min and a minimal fluid level of media in a dish (0.2 ml) and a treatment time of 10 seconds.

FIG. 2 shows plasma torch 102, which includes body 103. Body 103 houses gas fitting 104, BNC connector 105 and gas nozzle 109. A person having ordinary skill in the art appreciates that plasma torch 102 can be modified to accommodate different types of target cells and that the following description pertains to one example embodiment. It should be appreciated that body 103 can be made of aluminum or polytetrafluoroethylene stock or any other suitable alternative. Electrode 108 is connected internally to BNC connector 105 and is, preferably made of an approximately 0.02" diameter tinned copper wire with the tip machined to a point. In an example embodiment, electrode 108 includes a tinned copper wire having a diameter, which is 0.0253". BNC connector 105 can be operatively arranged to provide 50 Ohms resistance. Gas fitting 104 is preferably made of brass and threaded into body 103 and directs helium working gas 101 down acrylic nozzle 109 which houses electrode 108. Nozzle 109 has an inner diameter of approximately 0.125" and a length of approximately 3", preferably. In a preferred embodiment, the tip of electrode 108 is recessed approximately 0.04" from the end of acrylic nozzle 109. It should be appreciated that this arrangement provides the best helium/air mixture around the tip of electrode 108 for the flow rates described herein. When the tip of electrode 108 is at a sufficient potential, the electric field breaks down working gas 101 and plasma 100 is formed at the tip as shown in FIG. 3.

Figure 3:
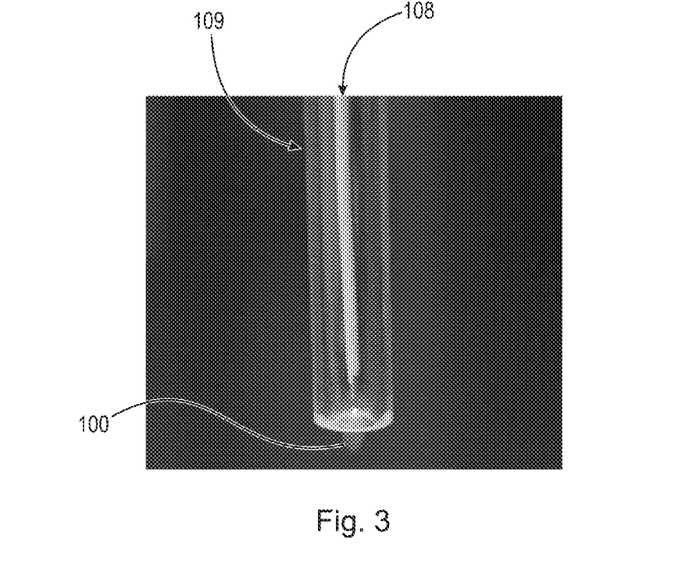
FIG. 3 is a photographic view of an example plasma jet protruding from the example torch nozzle shown in FIGS. 1 and 2.

The resultant plasma plume 100 generated by plasma torch 102 is shown in FIG. 3. It should be appreciated that the length of plasma jet 100 can vary depending on the flow rate of the helium working gas and can range between approximately 1 mm to approximately 7 mm. It should be appreciated that the lower the flow rate the harder it is to breakdown the gas because the contents in the atmosphere require a much higher breakdown voltage than helium. Generally, in ambient air without a sample or a dish, in order to produce a plasma jet of approximately 1 mm, the flow rate of the helium gas would be approximately 2.2 L/min. The flow rate of the working gas and the length of the plasma jet depend on the surrounding medium. As described above, in an example embodiment, the flow rate used with helium is 3-4.7 L/min and the minimal fluid level of media in a dish is 0.2 ml. The resulting plasma gas spreads out upon contact with a target surface. A person having ordinary skill in the art can determine to appropriate length of plasma jet 100 depending on the type of cancer being treated and the patient being treated. It should also be appreciated that torch 102 can be operated at low frequency in an example embodiment.

The plasma generation device described above produces reactive oxygen species, which can induce apoptosis and/or necrosis. Melanoma cells are susceptible to cell death by reactive oxygen species (ROS) due to their high intrinsic level of superoxide anions. In an example embodiment, a system is created whereby melanoma cells are saturated with ROS through treatment with non-thermal plasma (NTP) surpassing the antioxidant capacity of the cells and inducing alterations in cellular macromolecules including lipid peroxidation, DNA damage, and enzyme activation. NTP is formed from a mixture of highly charged helium and atmospheric gases to emit a total of 45 molecular species, many of which are ROS. NTP causes selective apoptotic cell death in melanoma cells as compared with normal skin keratinocytes in co-culture.

In an example embodiment, tirapazamine undergoes one-electron reduction to generate a radical. In the absence of oxygen, the radical undergoes spontaneous conversion to generate a benzotriazinyl radical, leading to DNA breaks and other complex lesions. When oxygen is present, tirapazamine undergoes futile cycling back to the parent compound with the concomitant formation of superoxide. A suitable enzyme catalyzes the one-electron reduction of tirapazamine. In an example embodiment, a two-electron reduction is contemplated. The two-electron reduction of tirapazamine is bioprotective to cells because it bypasses formation of the radical to generate the mono N-oxide, a relatively non-toxic metabolite. FIG. 4a through 7 demonstrate the selective apoptotic cell death in metastatic melanoma cells as compared with normal skin cells using non-thermal plasma.

Figure 4A:
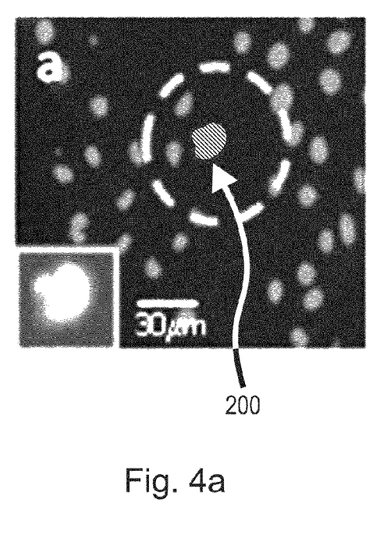
FIG. 4a shows co-cultured melanoma cells and normal skin keratinocytes before treatment of the non-thermal plasma of the invention.
Figure 4B:
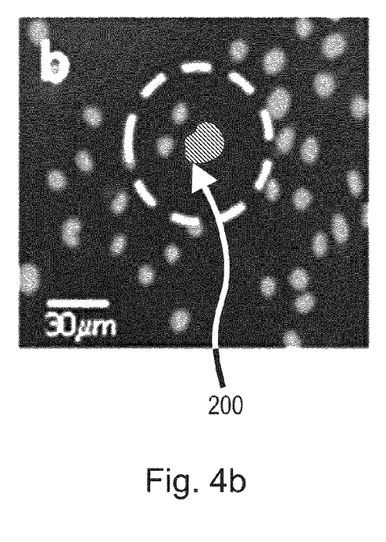
FIG. 4b shows the co-cultured melanoma cells and normal skin keratinocytes depicted in FIG. 4a after 1 minute of exposure to the non-thermal plasma of the invention.
Figure 4C:
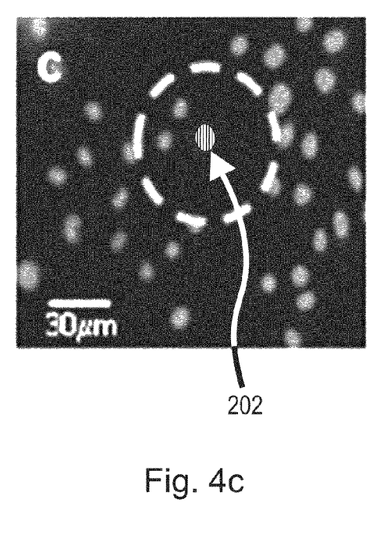
FIG. 4c shows the co-cultured melanoma cells and normal skin keratinocytes depicted in FIG. 4a after 5 minutes of exposure to the non-thermal plasma of the invention.

Melanoma cells can be transfected with a retroviral vector that links a gene of interest to green fluorescent protein (GFP) via an internal ribosome entry site to assure that all GFP expressing cells have the target gene. For example, the vector used can be the green fluorescent protein vector known in the art as pBMNIGFP. The vector can also include other transfectants. In a preferred embodiment, cells are stably transfected with wild type connexin 43 or a dominant negative to express different levels of gap junctions. FIGS. 4a, 4b, and 4c show melanoma cells co-cultured with normal skin keratinocytes seeded at a 1:25 ratio. The metastatic melanoma cells (referred to herein as 1205Lu) are sorted, for example, by flow cytometry, to express the green fluorescent protein. The keratinocytes are preferably not expressing fluorescent markers. Propidium iodide can be used to stain dead cells in red. Hoechst 33342 can be used to label DNA in cell nuclei in blue. Both can be added prior to treatment. FIG. 4a shows the co-cultured cells before treatment with the non-thermal plasma of the invention. GFP-expressing melanoma cell 200 is shown encircled by a broken circle. FIG. 4b shows the cells after 1 minute of exposure to the non-thermal plasma of the invention. A broken circle encompasses GFP-expressing melanoma cell 200.

FIG. 4c shows the cells after 5 minutes of plasma treatment. In FIG. 4c, encircled melanoma cell 202 is stained red with propidium iodide, for example, indicating that the melanoma cell (shown in green in FIGS. 4a and 4b) is killed after 5 minutes of exposure to the plasma treatment. FIG. 4c also shows the surrounding keratinocytes are not killed. As demonstrated, the plasma treatment can selectively kill melanoma cells that are surrounded by keratinocytes.

Figure 5:
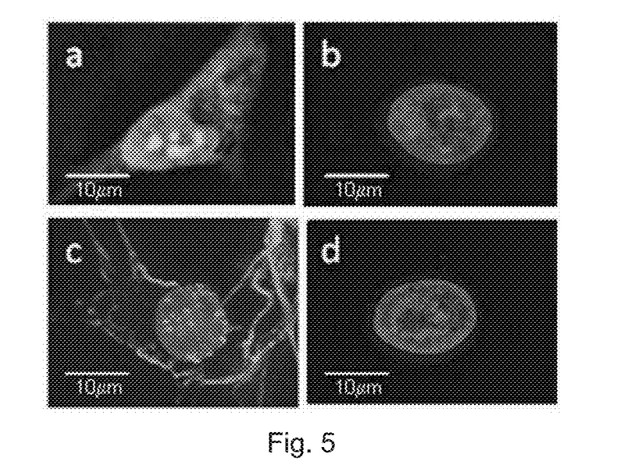
FIG. 5 shows the selective effect of the non-thermal plasma of the invention on melanoma cells versus normal skin keratinocytes.
Figure 6:
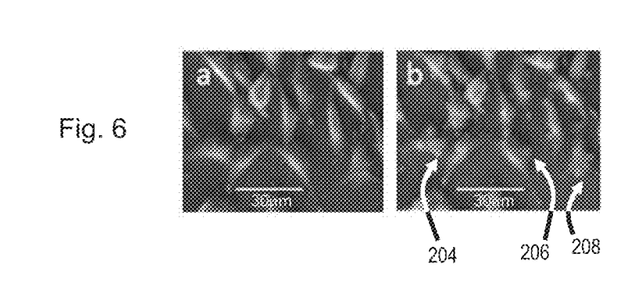
FIG. 6 shows the membrane blebbing and apoptosis caused by the non-thermal plasma of the invention on melanoma cells.
Figure 7:
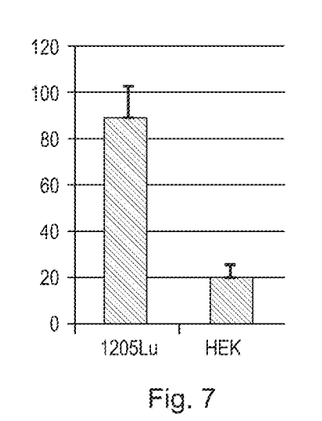
FIG. 7 shows a graphical representation of the selective effect of the non-thermal plasma of the invention on melanoma cells versus normal skin keratinocytes.

FIG. 5 shows melanoma cells in quadrants (a and c) and normal skin cells in quadrants (b and d). The melanoma cell shown in quadrant (a) is untreated whereas the melanoma cell shown in quadrant (c) is treated with plasma. In contrast, the normal epidural keratinocyte shown in quadrant (b) is untreated whereas the normal skin cell shown in quadrant (d) is treated with plasma. FIG. 6 shows induced extensions of the cell surface resembling membrane blebbing (204, 206 and 208). Such an effect is an early indication of apoptosis. After only 10 seconds of exposure to non-thermal plasma and 15 minutes of incubation, as is the case with FIG. 6, melanoma cells are targeted 59% as compared with the keratinocytes which are targeted only 8%. Quadrant (c) in FIG. 5 shows a melanoma cell 18 hours after exposure to plasma with fragmented DNA. Such DNA fragmenting is not present in the normal skin cell shown in quadrant (d) also 18 hours after exposure to plasma. It should be appreciated that a TUNEL assay can be used to assess apoptosis after plasma treatment. FIG. 7 shows percent of plasma-induced apoptosis (along the ordinate) between metastatic melanoma cells (1205Lu) and normal skin cells (HEK) (along the abscissa) based on the observations shown in FIGS. 5 and 6. In the graph shown in FIG. 7, approximately 20% of normal cells undergo plasma-induced apoptosis versus approximately 90% of melanoma cells.

Figure 8:
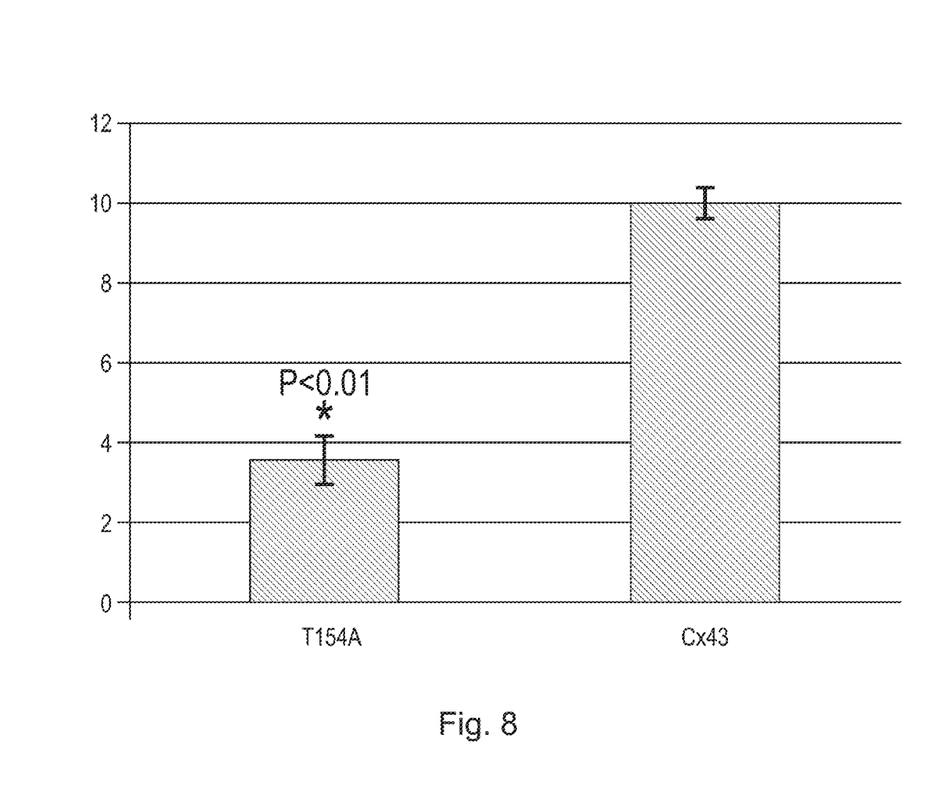
FIG. 8 shows a graphical representation of the increased cell death observed when active gap junctions are expressed as compared to when gap junctions are blocked.

In a preferred embodiment, in order to enhance the effects of non-thermal plasma, non-thermal plasma is combined with tirapazamine, which promotes cell toxicity through DNA damage only under hypoxic conditions. Gap junctions can act via the bystander effect to enable the passage of cell-death promoting signals by the non-thermal plasma. In the area next to the target site of the plasma, there is increased cell death when active gap junctions are expressed (Cx43) as compared to when gap junctions are blocked (T154A). FIG. 8 shows a graphical representation of percent cell death (along the ordinate) between premetastatic melanoma cells expressing dominant negative Cx43 (T154A) or wild type Cx43 (along the abscissa). The column on the left shows premetastatic melanoma cells expressing the dominant negative Cx43 (T154A) which blocks gap junctions. In contrast, the column on the right shows premetastatic melanoma cells expressing the wild type Cx43, which expresses active gap junctions. Clearly, the percent cell death is increased in premetastatic melanoma cells having expressed active gap junctions versus blocked gap junctions.

Figure 9:
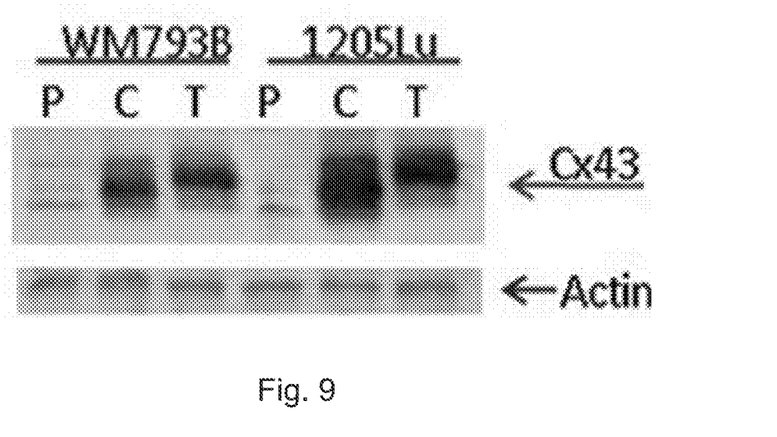
FIG. 9 shows the stable transfectants used in the invention.

FIG. 9 shows the development of wild type and dominant negative Cx43 melanoma cell lines. More specifically, premetastatic cells (WM793B) and metastatic cells (1205Lu) are each shown stably transfected with cells expressing plasmid alone (P), overexpressing connexin 43 (C), and overexpressing dominant negative connexin 43 (T).

Figure 10:
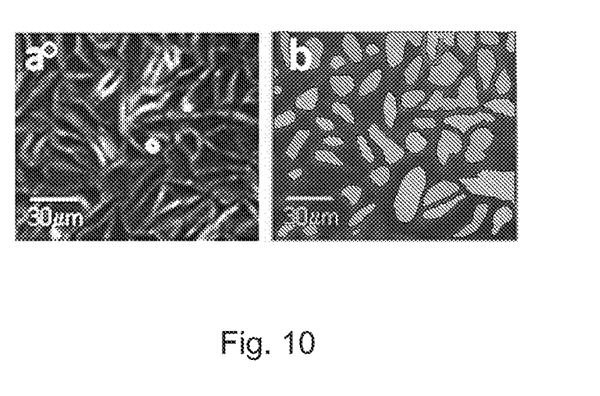
FIG. 10 shows cells expressed with green fluorescent protein.

FIG. 10 shows images of metastatic melanoma cells following stable transfection and cell sorting. The panel on the left shows 100% transfection efficiency under phase contrast; the panel on the right shows 100% transfection efficiency of these cells expressing the gene of interest (co-transfected with green fluorescent protein GFP) under fluorescence microscopy.

Figure 11:
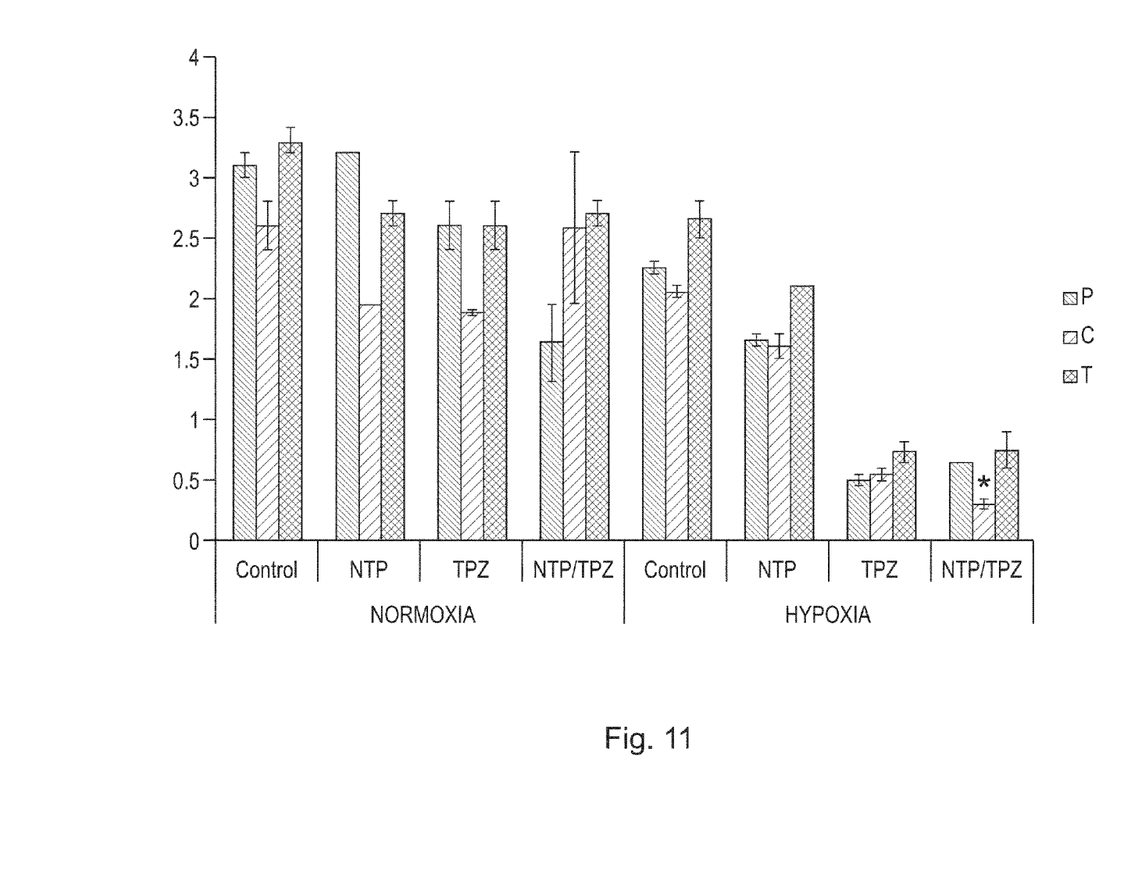
FIG. 11 shows a graphical representation of the effects of non-thermal plasma, tirapazamine, and non-thermal plasma and tirapazamine combined as compared with the control on cell viability under normoxia and hypoxia.

FIG. 11 shows a graphical representation of the number of viable cells compared for the following cell lines treated with non-thermal plasma only (NTP), tirapazamine only (TPZ), and the combination of non-thermal plasma and tirapazamine (NTP/TPZ) under the conditions of normoxia and hypoxia. The cell lines shown in FIG. 11 include: 1205Lu plasmid (P), 1205Lu Cx43 (C), 1205Lu-T154A (T). The abscissa shows the cell line and condition while the ordinate shows the number of viable cells (*$10^6$). The cells were treated with non-thermal plasma (NTP), tirapazamine at 28.5 μM (TPZ), or the combination (NTP/TPZ). Under normoxia, NTP caused a decrease in viable cells for 1205Lu Cx43 (C) and 1205Lu-T154A (T) but not for 1205Lu plasmid (P). Also under normoxia, TPZ caused a decrease in viable cells for all cell lines (P, C and T). NTP/TPZ caused a decrease in viable cells for 1205Lu plasmid (P) and 1205Lu-T154A (T) but not for 1205Lu Cx43 (C) under normoxia. Under hypoxia, all treatments (NTP, TPZ and NTP/TPZ) cause a decrease in cell number from the original number of cells ($6\times10^6$) to approximately ($3\times10^6$) for all melanoma cell lines. Under hypoxia, TPZ causes a decrease in cell number from the original number of cells ($6\times10^6$) to approximately ($1.2-0.6\times10^5$). Under hypoxia, NTP/TPZ causes a decrease from the original number of cells ($6\times10^6$) to approximately ($0.1-0.03\times10^5$). This shows a synergistic effect of non-thermal plasma and tirapazamine. Note the significant decrease in NTP/TPZ in the Cx43 cells (C).

The combination therapy with NTP and tirapazamine under hypoxic conditions causes a synergistic effect which increases cell death in all cells, yet is most apparent in the 1205Lu cells overexpressing the functional gap junctions. In addition, the target area of the NTP torch dramatically increases under these conditions. The ROS generated by NTP and tirapazamine induces the bystander effect and promotes the spreading of cell death signals well beyond the area of the plasma treatment. Upon treatment for 24 hours with NTP+/− tirapazamine at normal conditions (normoxia) or hypoxic conditions (hypoxia), the combination of NTP+/− tirapazamine enhances cell death under hypoxia. Furthermore, the area in which the plasma torch affects the cells increases only in the cells overexpressing the functional gap junctions. The total number of viable cells also significantly decreases with these conditions.

Figure 12:
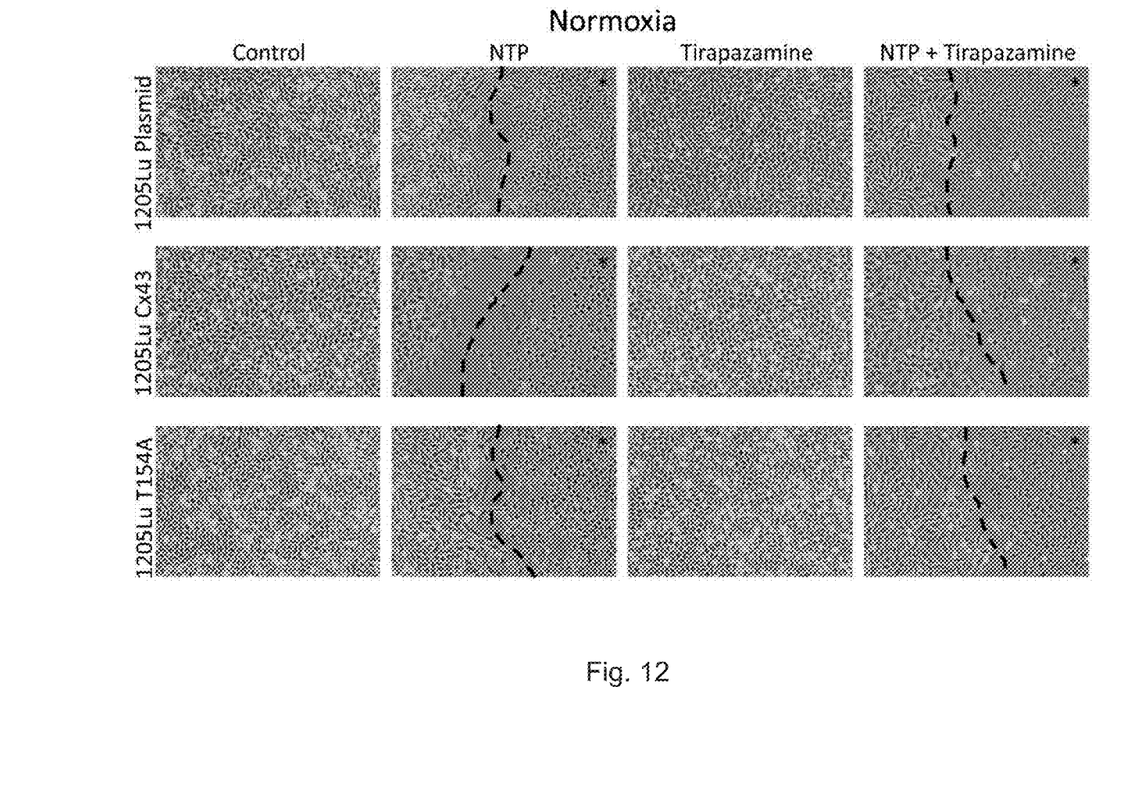
FIG. 12 shows photographic representations of cells under normoxia treated with non-thermal plasma, tirapazamine, and non-thermal plasma and tirapazamine combined as compared with the control.
Figure 13:
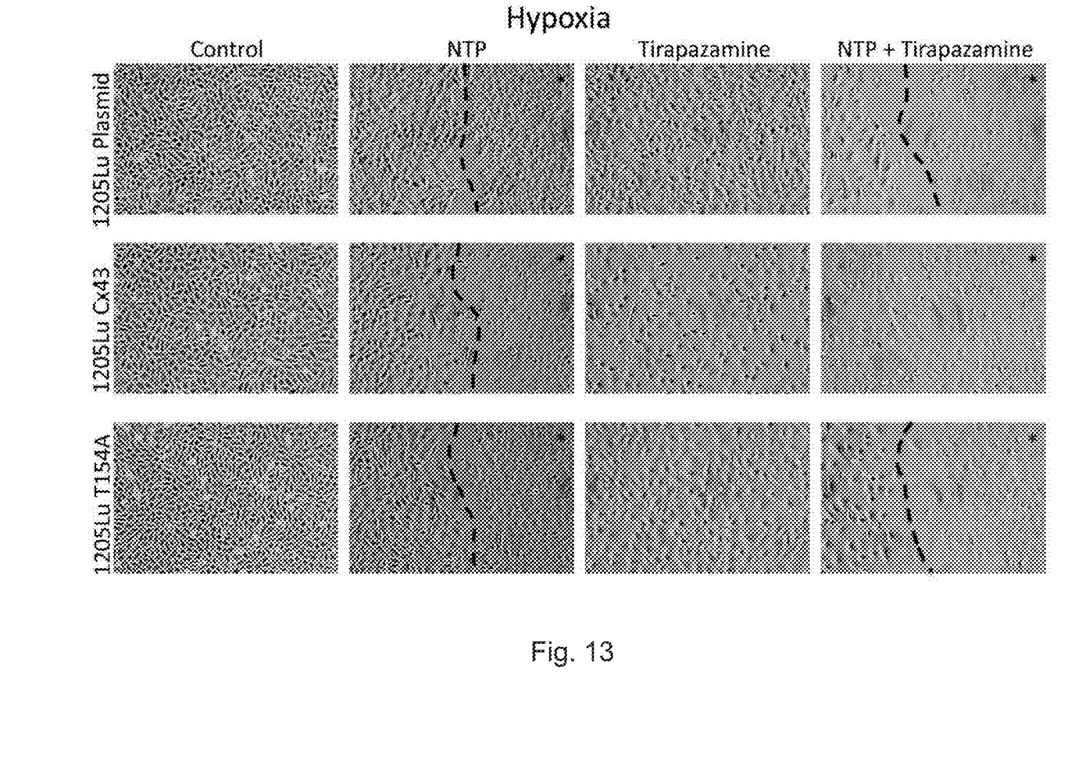
FIG. 13 shows photographic representations of cells under hypoxia treated with non-thermal plasma, tirapazamine, and non-thermal plasma and tirapazamine combined as compared with the control; and, FIG. 14 shows HIF1α expression under hypoxia and the effects of non-thermal plasma, tirapazamine, and non-thermal plasma and tirapazamine combined on HIF1α expression as compared with the control.

FIG. 12 shows photographically under normal oxygen conditions, tirapazamine has no effect, yet non-thermal plasma causes cell death at the target site, which is identified by the line separating NTP-targeted cells from viable cells. Tirapazamine induces cell toxicity only under hypoxic conditions and with non-thermal plasma as shown photographically in FIG. 13. Gap junction intercellular communication expands the area targeted by NTP. The broken lines shown in FIGS. 12 and 13 demarcate live cells from dead cells. The portions shown with asterisks represent the dead cells. In FIG. 13, under hypoxia, the cells with overexpressed gap junctions (120Lu Cx43) and treated with NTP/TPZ do not show a broken line because the extent of dead cells has spread throughout.

The overexpression of wild type connexin 43 (C) has the greatest effect on the treatment with NTP and tirapazamine, likely due to the bystander effect whereby the NTP/tirapazamine treatment produces radical species (ROS) that promote cell death and also pass through the gap junctions to increase the spreading of the cell death signals. FIG. 11 shows that both non-thermal plasma and tirapazamine cause cell death under low oxygen conditions and, in combination, they have a synergistic effect. This is particularly evident when gap junctions are overexpressed (1205Lu C×43).

While most tumor cells express low levels of gap junctions, it should be appreciated that this invention is not limited and includes all methods of modification of gap junctions by genetic, molecular manipulations as well as pharmaceutical treatment.

Figure 14:
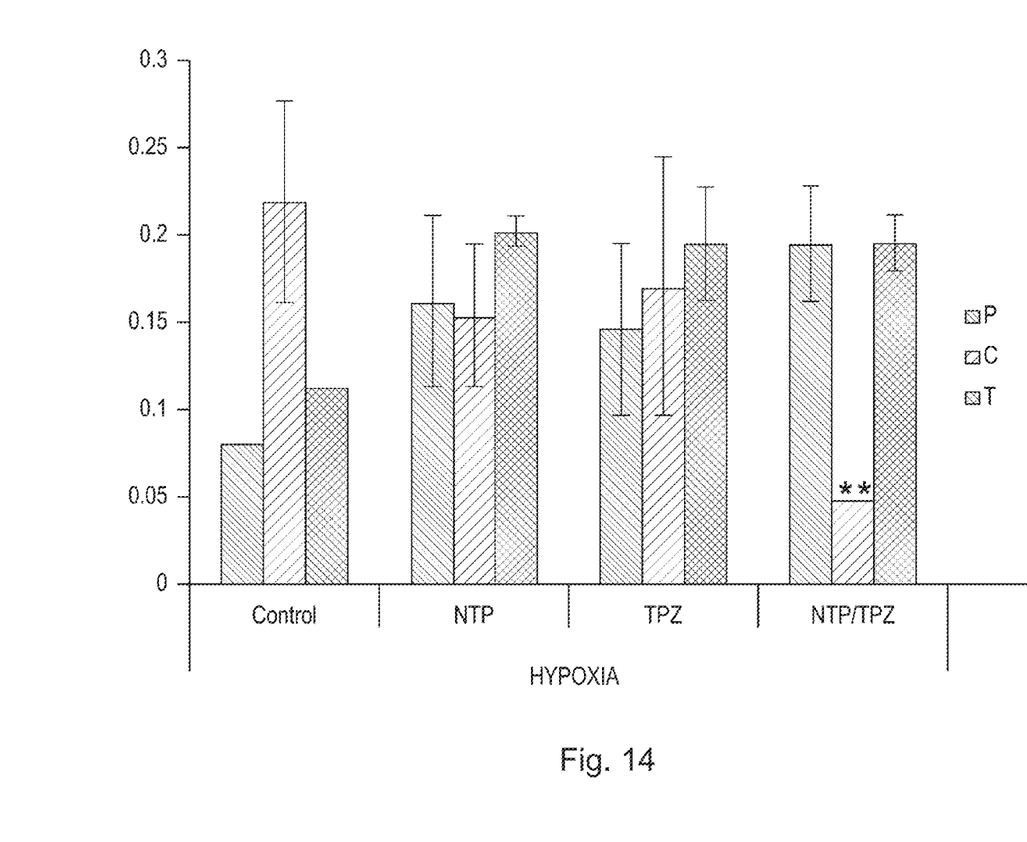

HIF1α is a transcription factor that enhances transcription of many metastasis related genes. The expression of HIF1α usually increases under hypoxic conditions. FIG. 14 shows the level of expression of HIF1α under hypoxia of cells lines P, C and T treated with NTP, TPZ or NTP/TPZ as compared with the control. Cell lines P and T, even treated with NTP, TPZ or NTP/TPZ, show an increase in the expression of HIF1α. In contrast, cell line C treated with NTP, TPZ or NTP/TPZ show a decrease in the expression of HIF1α. Moreover, the combination of NTP and tirapazamine exhibits an enhanced killing as compared with either treatment alone. This decrease could indicate a lower propensity to metastasize. The combination therapy causes increased cell death that is most pronounced if the melanoma cells have overexpressed gap junctions. These observations are further supported by the expression of HIF1α gene, which is enhanced under hypoxic conditions.

It should be appreciated that the combination therapy discussed herein can be implemented as follows. In an example embodiment, cancer cells can be manipulated to express increased gap junctions. In an example embodiment, a DNA damaging agent, for example, tirapazamine, is injected into the patient. In a preferred embodiment, the tirapazamine is used at the $IC_{50}$ for the 1205Lu melanoma cells (28.5 µm). A single injection can be a single dose of 10-40 mg/kg in a volume of 0.02 ml/g body weight. In an example embodiment, the tirapazamine solution is 50:50 v/v of dimethylsulfoxide (DMSO):saline. It should be appreciated that any other suitable dosage is contemplated. Thereafter, in an example embodiment, a non-thermal plasma is administered. The non-thermal plasma can be administered at single 10 or 20 sec treatments, for example, every second day with conditions of 87 kHz and 3 L/min flow rate at a 1 cm distance from the skin for 10 days. It should be appreciated that the non-thermal plasma can be administered at any appropriate time interval, for example, in a range of 5 to 30 seconds; more or less administration time may be appropriate in certain circumstances. Also, it should be appreciated that any other suitable administration is contemplated. For example, it should be appreciated that the non-thermal plasma is deliverable at a range of approximately 50-100 kHz at a flow rate of 3 L/min at approximately 1 cm from the tumor.

In an example embodiment, the cancer cells to be treated are at least approximately 150 $mm^3$ in diameter. Measuring tumors is a well-known technique in the art using calipers, for example. Calculating the tumor volume is also a well-known technique in the art using the formula V=0.5 a×b2 (a=long diameter of the tumor, b=short diameter of the tumor).

In an example embodiment, the non-thermal plasma is treated directly on the tumor via a device that is pre-sterilized under a UV lamp in a tissue culture hood. It should be appreciated that any other pre-sterilization method is contemplated. As described above, the plasma treatments are applied every other day. In an example embodiment, the frequency of the treatments is reduced over time.

Thus, the invention pertains to the combination of 1) non-thermal plasma treatment by any method of delivery including plasma torch, dielectrode barrier discharge (BDB), and any other suitable methods which are appreciable to a person having ordinary skill in the art as a means to deliver non-thermal plasma, and 2) tirapazamine and all structural and/or functional existing and future analogs that may be discovered and any drug which causes DNA damage and is activated under hypoxic (low oxygen conditions). Since most solid tumors exist under hypoxia, the drugs are designed to be activated in the tumor environment. The invention includes the combination of these drugs in any cellular (in vitro) treatment, in any animal models, and in any and all clinical use. The injections can be done via intraperitoneal in animals. Additionally, in animals, if the tumor reaches 2 $cm^3$ or if the animal experiences paralysis or some other major distress at 10 weeks from the first day of visible tumors the treatment should be discontinued and the animal euthanized according to procedures well known in the art.

It should be appreciated that a person having ordinary skill in the art can use the combination therapy described herein to treat other types of melanoma cancers and other types of non-skin-related cancers, even subcutaneous cancers. It should also be appreciated that the instant invention arose from a different way of comparing the viability of the combined therapy in cancer calls versus human skin cells. Typically, a therapy is tested in mouse models. Here, the combination therapy was initially tested using co-culture experiments with melanoma cells and normal skin cells. The melanoma cells were transfected to express the gap junction protein (C×43) or the empty plasmid (pBMN) and the green fluorescent protein (GFP) under the control of the same promoter as the gene of interest (C×43). Using this procedure, the DNA becomes integrated into the host's genome. Cell sorting can be used to achieve a pure, 100% GFP expressing cell population. This type of population is necessary to use in co-cultures with unlabeled normal cells.

It will be appreciated that various features of the above-described invention and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE NUMERALS

100 Non-thermal plasma
101 Helium gas
102 Torch
103 Body
104 Gas fitting
105 Connector
108 Electrode
109 Nozzle
110 Power supply
111 MOSFET
112 Functional generator
113 High frequency transformer
114 Coaxial connector cable
115 Voltage probe
116 Current probe
200 GFP expressing melanoma cell 202 Killed melanoma cell
204 Membrane blebbing
206 Membrane blebbing
208 Membrane blebbing

What is claimed is:

1. A composition of matter for treating cancer, comprising:
   a DNA-damaging agent deliverable to cancer cells at a treatment area and which activates only under a condition of hypoxia, and
   a non-thermal plasma deliverable to cancer cells at the treatment area;
   wherein said non-thermal plasma and said DNA-damaging agent individually and in conjunction promote cell activity.

2. The composition of matter for treating cancer as recited in claim 1, wherein said non-thermal plasma is generated from mixing helium gas and atmospheric gases and ionizing the mixed gases.

3. The composition of matter for treating cancer as recited in claim 1, wherein said DNA damaging agent is tirapazamine.

4. The composition of matter for treating cancer as recited in claim 1, wherein said cell toxicity is achieved via apoptosis.

5. The composition of matter for treating cancer as recited in claim 1, wherein said cell toxicity is achieved via necrosis.

6. The composition of matter for treating cancer as recited in claim 1, wherein said non-thermal plasma is deliverable via a plasma torch.

7. The composition of matter for treating cancer as recited in claim 1, wherein said DNA damaging agent is deliverable via injection.

8. The composition of matter for treating cancer as recited in claim 1, wherein said non-thermal plasma is deliverable via a plasma torch and said cancer is treated with said non-thermal plasma for at least one treatment which lasts for at least 10 seconds.

9. The composition of matter for treating cancer as recited in claim 1, wherein said cancer cells are manipulated to overexpress functional gap junctions.

10. The composition of matter for treating cancer as recited in claim 1, wherein said non-thermal plasma is deliverable via a plasma torch and said cancer is treated with said non-thermal plasma for at least one treatment which lasts for at least 20 seconds.

11. A method of treating melanoma in a patient using a combination therapy comprising the following steps:
    delivering a DNA-damaging agent to a treatment area, said DNA-damaging agent which activates only under a condition of hypoxia, and
    delivering a non-thermal plasma to said treatment area designated on said patient, said treatment area being infected with said melanoma.

12. The method of treating melanoma recited in claim 11, further comprising the step of delivering said DNA damaging agent via injection.

13. The method of treating melanoma recited in claim 11, wherein said DNA damaging agent is tirapazamine.

14. The method of treating melanoma recited in claim 11, further comprising the step of delivering said non-thermal plasma via at least one treatment, which lasts for at least 10 seconds.

15. The method of treating melanoma recited in claim 11, further comprising the step of delivering said non-thermal plasma directly on a tumor for at least one treatment, which lasts for at least 10 seconds.

16. The method of treating melanoma recited in claim 11, further comprising the step of delivering said non-thermal plasma via a plasma torch.

17. The method of treating melanoma recited in claim 11, further comprising the step of generating said non-thermal plasma by mixing helium gas and atmospheric gases and ionizing the mixed gases.

18. The method of treating melanoma recited in claim 11, further comprising the step of inducing cell toxicity via apoptosis.

19. The method of treating melanoma recited in claim 11, further comprising the step of inducing cell toxicity via necrosis.

* * * * *